(12) United States Patent
Cvetovich et al.

(10) Patent No.: US 7,022,841 B2
(45) Date of Patent: Apr. 4, 2006

(54) PROCESS FOR MAKING CARBAPENEM COMPOUNDS

(75) Inventors: Raymond Cvetovich, Scotch Plains, NJ (US); Robert Wenslow, East Windsor, NJ (US); John M. Williams, Belle Mead, NJ (US); Daniel Sidler, Whitehouse Station, NJ (US); Louis Crocker, Belle Mead, NJ (US); Hsien-Hsin Tung, Edison, NJ (US); Brian K. Johnson, Princeton, NJ (US); Joseph Kukura, II, Somerset, NJ (US); Ulf Dolling, Westfield, NJ (US)

(73) Assignee: Merck & Co. Inc., Rahway, NJ (US)

( * ) Notice: Subject to any disclaimer, the term of this patent is extended or adjusted under 35 U.S.C. 154(b) by 0 days.

(21) Appl. No.: 10/485,134

(22) PCT Filed: Sep. 20, 2002

(86) PCT No.: PCT/US02/29879

§ 371 (c)(1),
(2), (4) Date: Jan. 27, 2004

(87) PCT Pub. No.: WO03/027067

PCT Pub. Date: Apr. 3, 2003

(65) Prior Publication Data

US 2004/0176351 A1 Sep. 9, 2004

Related U.S. Application Data

(60) Provisional application No. 60/325,130, filed on Sep. 26, 2001.

(51) Int. Cl.
*C07D 477/20* (2006.01)

(52) U.S. Cl. ............... 540/350; 540/320; 540/351

(58) Field of Classification Search ............ 540/302, 540/350, 351
See application file for complete search history.

(56) References Cited

U.S. PATENT DOCUMENTS

| | | | |
|---|---|---|---|
| 4,888,344 A | 12/1989 | Sunagawa et al. | |
| 4,943,569 A | 7/1990 | Sunagawa et al. | |
| 5,478,820 A | 12/1995 | Betts et al. | |
| 5,872,250 A | 2/1999 | Williams et al. | |
| 6,180,783 B1 | 1/2001 | Williams et al. | |
| 2002/0128254 A1* | 9/2002 | Kawamoto et al. | 540/350 |
| 2004/0063931 A1* | 4/2004 | William et al. | 540/350 |
| 2004/0235817 A1* | 11/2004 | Brands | 540/350 |

FOREIGN PATENT DOCUMENTS

WO    WO02/57266 A1 *   1/2002

OTHER PUBLICATIONS

ICH Harmonized Tripartitle Guideline, Impurities: Guideline for Residual Solvents Q3C (1977), p. 1-16.*
Takeuchi et al., "The Stability of a Novel Carbapenem Antibiotic, Meropenem (SM-7338), in a Solid State Formulation for Injection", 1993, pp. 1998-2002vol. 41 (11), Chem. Pharm. Bull.
T.K. Natishan et al., "Residual Solvents Determination in the Antibiotic L-749,345 by Static Headspace Gas Chromatography", 1998, pp. 275-281, vol. 800, Journal of Chromatography A.

* cited by examiner

*Primary Examiner*—Mark L. Berch
(74) *Attorney, Agent, or Firm*—Sylvia A. Ayler; Valerie J. Camara

(57) ABSTRACT

The present invention relates to a process for reducing the levels of organic solvents to pharmaceutically acceptable levels in thermally unstable crystalline carbapenem solids represented by formula I:

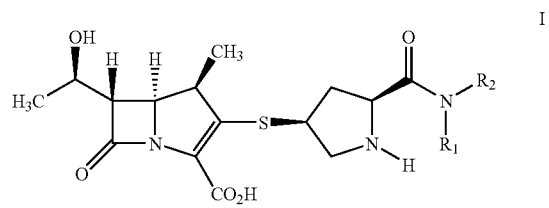

or a salt thereof, wherein $R_1$ and $R_2$, are the same or different, and are selected from H, alkyl, aryl, and heteroaryl, comprising washing a carbapenem solid containing organic solvent with an organic solvent containing water; and using vacuum and/or inert gas (hydrated or dry) at low temperature to produce a compound of formula I containing pharmaceutically acceptable levels of organic solvents, wherein the water content of the crystalline carbapenem solid, correcting for organic solvents, is maintained at about 13% to about 25% during the process.

21 Claims, 6 Drawing Sheets

PROCESS FOR MAKING CARBAPENEM COMPOUNDS

CROSS REFERENCE TO RELATED APPLICATIONS

This application is the National Stage of International Application No. PCT/US02/29879 filed on Sep. 20, 2002 which claims the benefit under 35 U.S.C. 119(e) of U.S. Provisional Application No. 60/325,130 filed on Sep. 26, 2001.

BACKGROUND OF THE INVENTION

Carbapenems are a broad class of antibiotic compounds useful for the treatment of infectious diseases including gram positive and negative, aerobic and anaerobic bacteria. U.S. Pat. No. 5,478,820 to Betts, assigned to Zeneca Ltd. teaches carbapenem compounds, salts and hydrolysable esters thereof, of the general formula:

useful as antibiotics, as well as a method for the preparation thereof.

Generally, organic solvents that are used in the crystallization of carbapenem compounds are difficult to remove from the final product because of the limited stability of the compounds. See Takeuchi, Y. et al., Chem. Pharm. Bull. Vol. 41, No. 11, 1993, pg. 1998–2002. These solvents must be reduced to levels that are acceptable for pharmaceutical use. The pharmaceutically acceptable level depends upon the solvent and the maximum daily dose to be administered. Guidelines for what is acceptable are provided by the International Conference on Harmonisation (ICH). For the organic solvents that would be used in pharmaceutical processing and for doses typically used in treatment of bacterial infection, the pharmaceutically acceptable limit would be about 2%. The reduction of organic solvents to pharmaceutically acceptable levels can sometimes be accomplished by heating a compound under vacuum or in a stream of inert gas. However, the process of heating can result in significant degradation of these thermally unstable compounds.

In the present case, the carbapenem solids isolated by crystallization from water/alcohol mixtures become amorphous when the water content of the solid is reduced below a certain level. The organic solvent remaining on the solid when it becomes amorphous is not readily removed and remains above the pharmaceutically acceptable limit. This invention relates to a process for reducing the levels of organic solvents in crystalline carbapenem solids while minimizing degradation of the thermally unstable antibiotic to give a product that is acceptable for pharmaceutical use.

SUMMARY OF THE INVENTION

A process for reducing the levels of organic solvents in thermally unstable crystalline carbapenem solids to pharmaceutically acceptable levels, comprising washing a carbapenem solid of formula I:

containing organic solvent with an organic solvent containing water to produce a washed carbapenem solid containing residual organic solvent, and evaporating the residual organic solvent in the washed carbapenem solid using vacuum and/or inert gas at low temperature to produce a carbapenem solid of formula I or a salt thereof, containing pharmaceutically acceptable levels of organic solvents, wherein the water content of the carbapenem solids, correcting for organic solvent, is maintained at about 13% to about 25% during the process, wherein $R_1$ and $R_2$ are the same or different and are selected from H, alkyl, aryl, and heteroaryl, said alkyl, aryl and heteroaryl optionally substituted.

A second aspect of the invention relates to a crystalline form, Form C, produced in the process. The levels of residual organic solvents are more readily reduced in solids containing this crystalline form, thereby minimizing degradation incurred in the process. A method of preparation of said crystal form is also disclosed. This and other aspects of the invention are realized upon an in depth review of the specification as a whole.

BRIEF DESCRIPTION OF THE DRAWINGS

The invention is described in connection with the following figures, of which.

DETAILED DESCRIPTION OF THE INVENTION

In one embodiment of the invention there is disclosed a process for reducing the levels of organic solvents in a carbapenem solid of formula I:

or salts thereof, wherein $R_1$ and $R_2$ are the same or different and are selected from H, alkyl, aryl, and heteroaryl, said alkyl, aryl and heteroaryl optionally substituted, comprising the steps of:
a) washing the carbapenem solid containing organic solvent with an organic solvent containing water to produce a washed carbapenem solid containing residual organic solvent; and
b) evaporating the residual organic solvent in the washed carbapenem solid using vacuum and/or inert gas at low temperature to produce a compound of formula I containing pharmaceutically acceptable levels of organic solvents.

In a sub-embodiment of this invention there is disclosed a process wherein $R^1$ and $R^2$ are defined to give the compound of formula II:

wherein $X^+$ is selected from $Na^+$, $K^+$ and $Li^+$.

As utilized herein, the term "alkyl" refers to a monovalent alkane (hydrocarbon) straight, branched or cyclic substituents with 1 to 15 carbon atoms unless otherwise defined. Preferred straight or branched alkyl groups include methyl, ethyl, propyl, isopropyl, butyl and t-butyl. Preferred cycloalkyl groups include cyclopropyl, cyclopentyl and cyclohexyl. Alkyl also includes an alkyl group substituted with a cycloalkyl group such as cyclopropylmethyl.

Alkyl also includes a straight or branched alkyl group which contains or is interrupted by a cycloalkylene portion. Examples include the following:

wherein: x' and y'=from 0–10; and w and z=from 0–9.

When substituted alkyl is present, this refers to a straight, branched or cyclic alkyl group as defined above, substituted with 1–3 groups as defined with respect to each variable.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl and naphthyl substituted with one to three groups.

The term "heteroaryl" refers to a monocyclic aromatic hydrocarbon group having 5 to 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups.

Heteroaryl includes aromatic and partially aromatic groups which contain one or more heteroatoms. Examples of this type are thiophene, purine, imidazopyridine, pyridine, oxazole, thiazole, oxazine, pyrazole, tetrazole, imidazole, pyridine, pyrimidine, pyrazine and triazine. Examples of partially aromatic groups are tetrahydroimidazo[4,5-c]pyridine, phthalidyl and saccharinyl, as defined below.

Substituted alkyl, aryl and heteroaryl, and the substituted portions of aralkyl, aralkoxy, heteroaralkyl, heteroaralkoxy and like groups are substituted with from 1–3 groups selected from the group consisting of: halo, hydroxy, cyano, acyl, acylamino, aralkoxy, alkylsulfonyl, arylsulfonyl, alkylsulfonylamino, arylsulfonylamino, alkylaminocarbonyl, alkyl, alkoxy, aryl, aryloxy, aralkoxy, amino, alkylamino, dialkylamino, carboxy, trifluoromethyl, carbamoyloxy $C_{1-6}$ alkyl, ureido $C_{1-6}$ alkyl, carbamoyl, carbamoyl $C_{1-6}$ alkyl or mono- or di-$C_{1-6}$ alkyl carbamoyl $C_{1-6}$ alkyl and sulfonylamino.

$X^+$ is a charge-balancing group selected from $Na^+$, $K^+$ and $Li^+$, preferably $Na^+$.

The salts included within the invention are those known in the art to be acceptable for pharmaceutical use.

A wide range of organic solvents can be reduced to pharmaceutically acceptable levels by this process including $C_1$ to $C_5$ alcohols such as methanol, ethanol, 1-propanol, 2-propanol, and the like, $C_3$ to $C_8$ esters or ketones such as methyl acetate, ethyl acetate, isopropyl acetate, acetone, methyl ethyl ketone and the like, ethers such as tetrahydrofuran and dioxane, amides such as dimethylformamide and dimethylacetamide, and nitriles such as acetonitrile and propionitrile, or a mixture thereof. Typically, organic solvents are those used in crystallization of the carbapenem or in washing the product to remove impurities. The preferred solvents are methanol, ethanol, 1-propanol, and 2-propanol or a mixture thereof, with the most preferred being methanol, 1-propanol, and 2-propanol.

For purposes of this invention organic solvents containing water that are useful in washing the carbapenem solids allowing solvent reduction at low temperature include volatile, non-hydroxylic solvents such as methyl acetate, acetonitrile, tetrahydrofuran, and acetone or a mixture thereof containing 1–5% (w/v) water. Preferred is methyl acetate containing about 2 to about 4% (w/v) water. A compound of formula II forms a crystalline hydrate when washed with these solvents containing water.

For purposes of this invention residual organic solvents are those organic solvents remaining on the carbapenem solid after the wash step such as $C_1$ to $C_5$ alcohols (e.g., methanol, ethanol, 1-propanol, 2-propanol, and the like), $C_3$ to $C_8$ esters or ketones (e.g., methyl acetate, ethyl acetate, isopropyl acetate, acetone, methyl ethyl ketone and the like), ethers (e.g., tetrahydrofuran and dioxane), amides (e.g., dimethylformamide and dimethylacetamide), and nitriles (e.g., acetonitrile and propionitrile), or a mixture thereof.

For purposes of this invention the term organic solvent or organic solvents refer to one or more organic solvents.

The term "hydrate" is used in the conventional sense to represent compounds of the invention associated with water. For purposes of this invention, residual organic solvent reduction is conducted such that the water content of the carbapenem compound, correcting for organic solvents, is maintained at about 13–25%, preferably 16–22%.

One or more embodiments of this invention are those that relate to a process wherein:

the temperature of the carbapenem solids is about –15° C. to about 20° C.;

reduction in the levels of organic solvents is conducted using vacuum and/or an inert gas at temperatures below about 0° C., a subset of the reduction process is maintaining the water content of the solids at about 13% to about 25%, preferably about 16% to about 22%;

reduction in the levels of organic solvents is conducted using a hydrated inert gas at temperatures below about 20° C., a subset of the reduction process is maintaining the water content of the solids at about 13% to about 25%, preferably about 16% to about 22%;

reduction in the levels of organic solvents is conducted using vacuum and a hydrated inert gas at temperatures below about 20° C., a subset of the reduction process is maintaining the water content of the solids at about 13% to about 25%, preferably about 16% to about 22%;

the inert gas is nitrogen and the flow rate of the gas is about 0.3 to about 30 SLPH (standard liters/hour)/assay gram of Compound II; and the organic solvent containing water and used in washing the carbapenem solids is selected from the group consisting of methyl acetate, acetonitrile, tetrahydrofuran, and acetone or a mixture thereof. The methyl acetate, acetonitrile, tetrahydrofuran, acetone or mixture thereof generally contains about 1% to about 5% (w/v) water, preferably about 2 to about 4% (w/v) water.

A preferred aspect of this invention is a process for the reduction of organic solvents in carbapenem solid (4R, 5S, 6S, 8R, 2'S, 4'S)-3-[[2-[[3-carboxyphenyl)amino]carbonyl]pyrrolidin-4-yl]thio]-4-methyl-6-(1-hydroxyethyl)-7-oxo-1-azabicyclo[3.2.0]hept-2-en-2-carboxylic acid sodium salt represented by the compound of formula IIa:

IIa comprising the steps of:

a) washing the carbapenem solid of formula IIa containing organic solvent with methyl acetate containing about 1% to about 5% (w/v) water to produce a washed carbapenem solid of formula IIa; and b) evaporating the residual organic solvent in the washed carbapenem solid of formula IIa using vacuum and hydrated nitrogen at a nitrogen flow rate of about 0.3 to about 30 SLPH (standard liters/hour)/assay gram of the compound and a temperature of about 10° C. or below to produce a compound of formula IIa containing pharmaceutically acceptable levels of organic solvents.

Another aspect of this invention relates to a process wherein the organic solvent is selected from the group consisting of methanol, ethanol, 1-propanol, and 2-propanol.

Another aspect of this invention is realized when the methyl acetate contains about 2 to about 4% (w/v) water.

Still another aspect of the invention relates to a process wherein the water content of the carbapenem compound during residual organic solvent reduction is maintained at about 13% to about 25%.

Still another aspect of this invention relates to a process wherein the inert gas stream used in residual solvent reduction is hydrated such that the water content of the solid is maintained at about 16% to about 22% during the residual organic solvent reduction operation.

Figure 5:
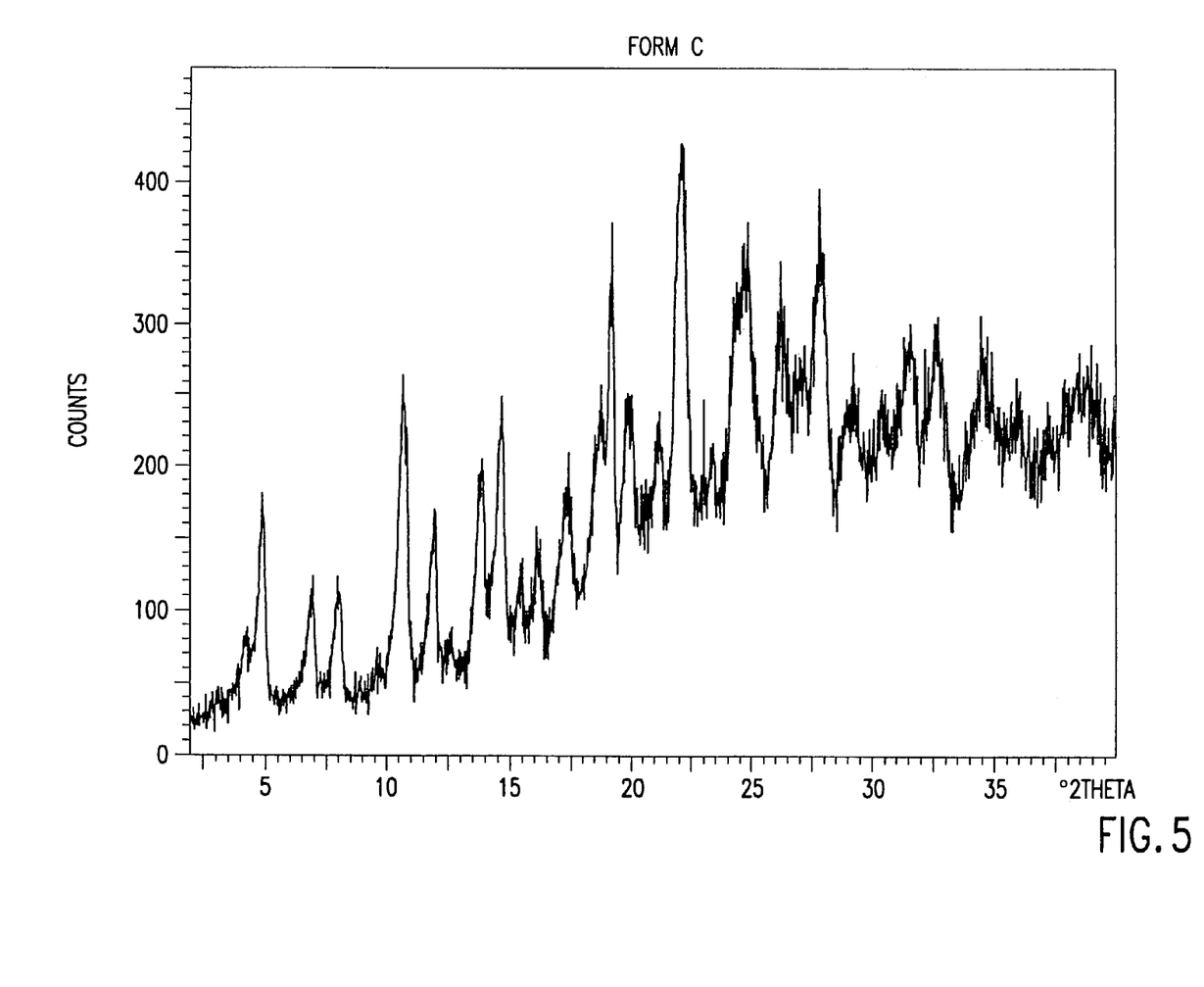
FIG. 5 is an X-Ray Powder Diffraction pattern for crystal Form C of Compound IIa resulting from washing the solid containing crystal Form B of the Compound IIa with methyl acetate containing 2% (w/v) water.

This invention also relates to a process for the reduction of residual organic solvent in carbapenem solid (4R, 5S, 6S, 8R, 2'S, 4'S)-3-[[2-[[3-carboxyphenyl)amino]-carbonyl]pyrrolidin-4-yl]thio]-4-methyl-6-(1-hydroxyethyl)-7-oxo-1-azabicyclo[3.2.0]hept-2-en-2-carboxylic acid sodium salt of Form C as characterized by the XRPD pattern depicted in FIG. 5 and represented by formula IIa:

IIa comprising evaporating the residual organic solvent using vacuum and a hydrated nitrogen stream at a flow rate of about 0.3 to about 30 SLPH (standard liters/hour)/assay gram of the compound and a temperature of about 10° C. or below to produce a compound of formula IIa containing pharmaceutically acceptable levels of organic solvents.

A sub-embodiment of this invention relates to a process wherein the residual organic solvent is selected from the group consisting of methanol, ethanol, 1-propanol, 2-propanol, methyl acetate, acetonitrile, tetrahydrofuran, and acetone or a mixture thereof.

Another sub-embodiment of the invention relates to a process wherein the water content of the carbapenem solids during residual organic solvent reduction is maintained at about 13% to about 25%.

Still another sub-embodiment of this invention relates to a process wherein the inert gas stream used in residual organic solvent reduction is hydrated such that the water content of the solid is maintained at about 16% to about 22% during the residual organic solvent reduction operation.

Generally, the compounds of formula I, II, IIa can be synthesized in accordance with U.S. Pat. No. 4,888,344, issued on Jul. 24, 1990 to M. Sunagawa, U.S. Pat. Nos. 4,943,569, U.S. Pat. No. 6,180,783, issued Jan. 30, 2001, U.S. Pat. No. 5,872,250, issued Feb. 16, 1999 as well as U.S. Pat. No. 5,478,820, issued Dec. 26, 1995 to Betts et al., all incorporated herein by reference thereto.

According to one method of preparation, the compound of formula IIa can be prepared as illustrated in the following non-limiting scheme:

The process of this invention is characterized by washing the carbapenem solids containing organic solvents with a mixture of, for example, methyl acetate and water to produced a washed carbapenem solid containing, for example, residual methyl acetate. Residual methyl acetate in the solid can then be reduced to a pharmaceutically acceptable level at low temperature by passing a stream of inert gas (hydrated or dry) through the solids, or by subjecting the solids to vacuum with or without a stream of inert gas (hydrated or dry). Different combinations of conditions provide the desired result as long as the water content of the carbapenem solids is maintained between about 13 and 25% (correcting for residual organic solvent). For example, the water content of the solvent/water mixture can be defined to give a sufficiently high water content in the solids (up to about 25% correcting for residual organic solvent) such that residual organic solvents can be reduced to pharmaceutically acceptable levels using vacuum alone or a dry inert gas stream. In this case, the temperature of the solid is controlled at below about 0° C. to ensure selective removal of the organic solvent. Alternatively, the gas used in residual organic solvent reduction can be hydrated to maintain the water content of the solid above about 13% (correcting for residual organic solvent) during the residual organic solvent reduction operation. Using hydrated inert gas, with or without vacuum, allows reduction in residual organic solvents to pharmaceutically acceptable levels at temperatures up to about 20° C.

Generally, the washing is conducted with a mixture of a volatile, non-hydroxylic water miscible organic solvent and water. Preferred organic solvents are acetone and methyl acetate. The amount of wash is generally about 10 to about 30 mL/g. The temperature of the solids during the wash operation is generally about −15° C. to about 20° C., preferably about 0° C. to about 10° C.

The pharmaceutically acceptable level or levels depends upon the solvent or solvents contained in the washed carbapenem solid, particularly since each solvent may have a different pharmaceutically acceptable limit. However, the pharmaceutically acceptable limit for the carbapenem solid as a whole would be about 2%.

Gases that can be used in the process include those gases that would be considered inert or unreactive toward the carbapenem product including but not limited to those that are commonly used in pharmaceutical processing such as nitrogen and argon. The preferred inert gas is nitrogen.

As would be understood by a person of ordinary skill in the art, the time required for residual organic solvent reduction is dependent upon cake height, gas flow, vacuum, and temperature and ranges from about one half hour to about 96 hours. When a gas such as nitrogen is passed through the solid in residual organic solvent reduction, the gas flow rate is generally about 0.3 to 30 SLPH/assay gram where gas flow is represented in standard liters per hour. The rate of residual organic solvent removal increases with gas flow rate. The highest practical flow rate, therefore, affords the fastest residual organic solvent reduction. When vacuum is used, the rate of residual organic solvent reduction increases with increasing vacuum. The highest practical vacuum, therefore, affords the fastest residual organic solvent reduction. The fastest rate is achieved using a combination of vacuum level and gas flow through the solid. In this case, the gas flow ranges from 0.3 to 30 SLPH/assay gram of the compound where gas flow is represented in standard liters per/hour. The operation is generally conducted at a temperature of about −10° C. to about 20° C., preferably about 0° C. to about 10° C. The humidity of the gas stream used in residual organic solvent reduction is controlled such that the dew point of the gas is maintained at least 2° C. below the temperature of the solid to avoid condensation.

In a preferred process, the carbapenem solids containing organic solvent are first washed with an organic solvent containing water (such as methyl acetate containing 2–4% (w/v) water) followed by reduction in the level of the organic solvent used in washing the solids using vacuum and hydrated nitrogen while maintaining the solid temperature below about 10° C. By subjecting these solids to conditions which reduce the levels of residual organic solvents but maintain the water content of the solids in the range from about 13% to about 25%, the residual organic solvents are more readily reduced to pharmaceutically acceptable levels.

This invention also relates to a process which comprises washing the carbapenem solids containing organic solvent first with an anhydrous solvent such as methanol, ethanol, 1-propanol, 2-propanol, methyl acetate, acetone, or the like, which produces an amorphous solid. The residual organic solvent levels in this amorphous material can then be reduced to pharmaceutically acceptable levels by using a hydrated gas such as nitrogen in the process thereby increasing the water content of the solids.

The invention also relates to a crystalline hydrate, Form C, of (4R, 5S, 6S, 8R, 2'S, 4'S)-3-[[2-[[3-carboxyphenyl)amino]carbonyl]pyrrolidin-4-yl]thio]-4-methyl-6-(1-hydroxyethyl)-7-oxo-1-azabicyclo[3.2.0]hept-2-en-2-carboxylic acid monosodium salt which can be represented by the following formula:

IIa and a process for making the same comprising washing a crystalline form, Form A or Form B, of the compound of formula IIa with an organic solvent selected from methyl acetate, acetonitrile, tetrahydrofuran, acetone or a mixture thereof containing water.

A sub-embodiment of this invention is realize when the crystalline compound is Form B and the organic solvent used in washing the carbapenem solids is methyl acetate containing 2–4% water.

The crystalline Form C of the compound of formula IIa described herein is a hydrate in which water is weakly bound. This crystalline form is not thermally stable and does not exhibit a distinct, well-defined melting point, but rather undergoes decomposition with loss of water upon heating.

The crystalline form is characterized below by virtue of X-Ray Powder Diffraction (XRPD) pattern and solid-state nuclear magnetic resonance (NMR) spectrum, which are useful in unambiguously identifying the unique form disclosed herein. The XRPD pattern was collected on a Philips automated powder diffractometer with XRG 3100 control and PW3710 mpd control using CuKα radiation with an accelerating potential of 45 kV and a filament emission of 40 mA. The diffraction pattern was collected from about 2 to about 40 °2Theta. The solid-state NMR spectrum was generated using a Bruker DSX 400WB NMR system operating at 100.6 MHz for $^{13}$C and 400.1 MHz for $^{1}$H using a Bruker MAS 400WB BL7 double-resonance probe with a spinning module housing a 7 mm zirconia rotor with either KEL-F® end caps with a liquid seal plug or zirconia endcaps. The solid-state $^{13}$C NMR spectrum was acquired using cross polarization (CP), magic-angle spinning (MAS), and high-power decoupling. Proton and carbon 90° pulse widths were ~4 μsec with a contact time of 2.0 msec. The sample was spun at 7.0 kHz and a total of 600–800 scans were collected with a recycle delay of 7.0 sec. Sample temperature between –20 and –5° C. A line broadening of 10 Hz was applied before FT was performed. Chemical shifts are reported on the TMS scale using the carbonyl carbon of glycine (176.03) as a secondary reference.

Form A:

The crystalline Form A of the compound of formula IIa is formed through crystallization from or contact with a mixture of water, methanol, and 1-propanol. This form is unambiguously characterized as having the XRPD pattern 18.44, 13.09, 8.43, 7.58, 6.48, 6.16, 5.55, 5.14, 4.81, 4.50, 4.26, 4.11, 4.02, 3.85, 3.69, 3.41, 3.35, 3.03, 3.25, 3.12, and 2.87 angstroms. More complete XRPD data pertaining to the compound is shown below in Table 1.

TABLE 1

XRPD pattern for the compound of formula IIa crystallized from a mixture of water, methanol, and 1-propanol (Form A).

| Angle (°2Theta) | D Spacing (angstroms) | I/Imax (%) |
|---|---|---|
| 4.8 | 18.44 | 100 |
| 6.7 | 13.09 | 41 |
| 10.5 | 8.43 | 38 |
| 11.7 | 7.58 | 41 |
| 13.6 | 6.48 | 72 |
| 14.4 | 6.16 | 62 |
| 16.0 | 5.55 | 39 |
| 17.2 | 5.14 | 44 |
| 18.4 | 4.81 | 63 |
| 19.7 | 4.50 | 60 |
| 20.8 | 4.26 | 64 |
| 21.6 | 4.11 | 59 |
| 22.1 | 4.02 | 66 |
| 23.1 | 3.85 | 63 |
| 24.1 | 3.69 | 93 |
| 26.1 | 3.41 | 83 |
| 26.6 | 3.35 | 67 |
| 27.0 | 3.03 | 71 |
| 27.4 | 3.25 | 71 |
| 28.6 | 3.12 | 63 |
| 31.1 | 2.87 | 83 |

Figure 1:
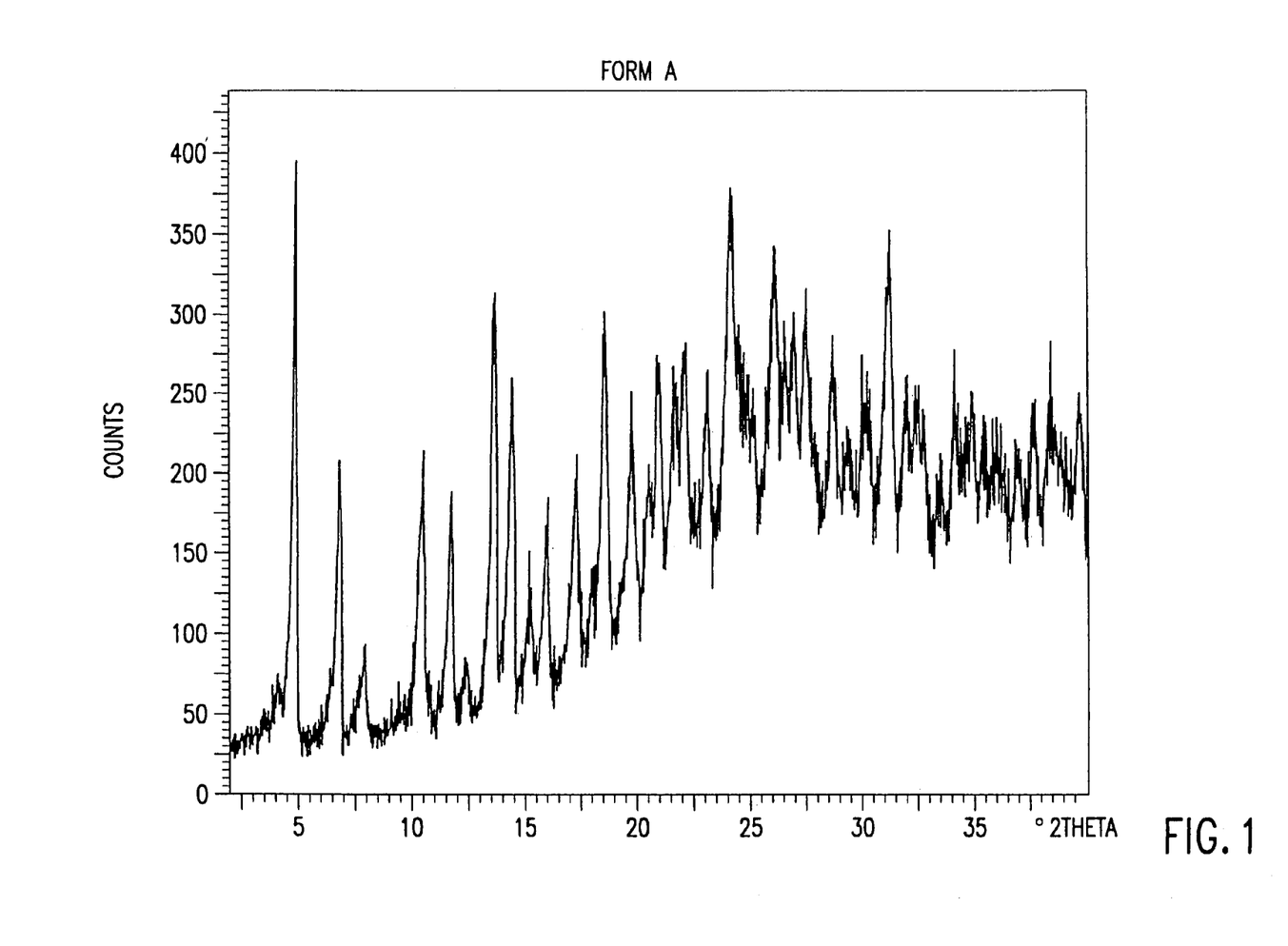
FIG. 1 is the X-Ray Powder Diffraction pattern for crystal Form A of Compound IIa crystallized from a mixture of water, methanol, and 1-propanol.

The XRPD pattern corresponding to Table 1 is shown in FIG. 1.

Figure 2:
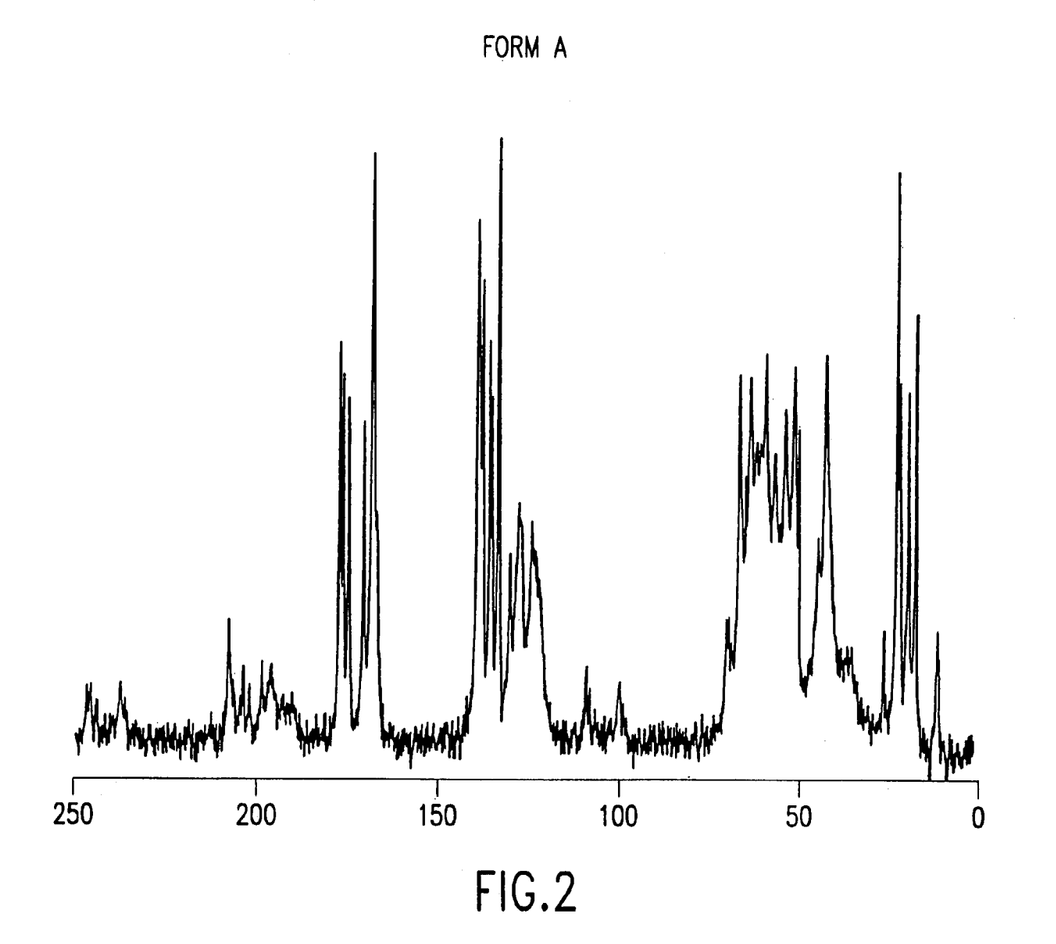
FIG. 2 is the solid-state NMR spectrum for crystal Form A of Compound IIa crystallized from a mixture of water, methanol, and 1-propanol.

The solid-state NMR pattern corresponding to Form A is shown in FIG. 2.

Form B:

The crystalline Form B of the compound of formula IIa is formed through contact of the compound with a mixture of water and 2-propanol and is unambiguously characterized as having the XRPD pattern 18.48, 13.02, 11.27, 8.50, 7.51, 6.51, 6.13, 5.82, 5.13, 4.78, 4.67, 4.50, 4.24, 4.06, 3.85, 3.69, 3.63, 3.41, 3.36, 3.31, 3.22, 3.11, 2.98, 2.87, and 2.77 angstroms. More complete XRPD data pertaining to the compound is shown below in Table 2.

TABLE 2

XRPD pattern for the compound of formula IIa contacted with a mixture of water and 2-propanol (Form B).

| Angle (°2Theta) | D Spacing (angstroms) | I/Imax (%) |
|---|---|---|
| 4.8 | 18.48 | 59 |
| 6.8 | 13.02 | 24 |
| 7.8 | 11.27 | 21 |
| 10.4 | 8.50 | 49 |
| 11.8 | 7.51 | 34 |

TABLE 2-continued

XRPD pattern for the compound of formula IIa contacted with a mixture of water and 2-propanol (Form B).

| Angle (°2Theta) | D Spacing (angstroms) | I/Imax (%) |
|---|---|---|
| 13.6 | 6.51 | 55 |
| 14.4 | 6.13 | 51 |
| 15.2 | 5.82 | 27 |
| 17.3 | 5.13 | 32 |
| 18.5 | 4.78 | 58 |
| 19.0 | 4.67 | 64 |
| 19.7 | 4.50 | 62 |
| 20.9 | 4.24 | 58 |
| 21.9 | 4.06 | 100 |
| 23.1 | 3.85 | 39 |
| 24.1 | 3.69 | 46 |
| 24.5 | 3.63 | 65 |
| 26.1 | 3.41 | 51 |
| 26.5 | 3.36 | 37 |
| 26.9 | 3.31 | 34 |
| 27.7 | 3.22 | 75 |
| 28.7 | 3.11 | 32 |
| 30.0 | 2.98 | 33 |
| 31.1 | 2.87 | 47 |
| 32.3 | 2.77 | 49 |

Figure 3:
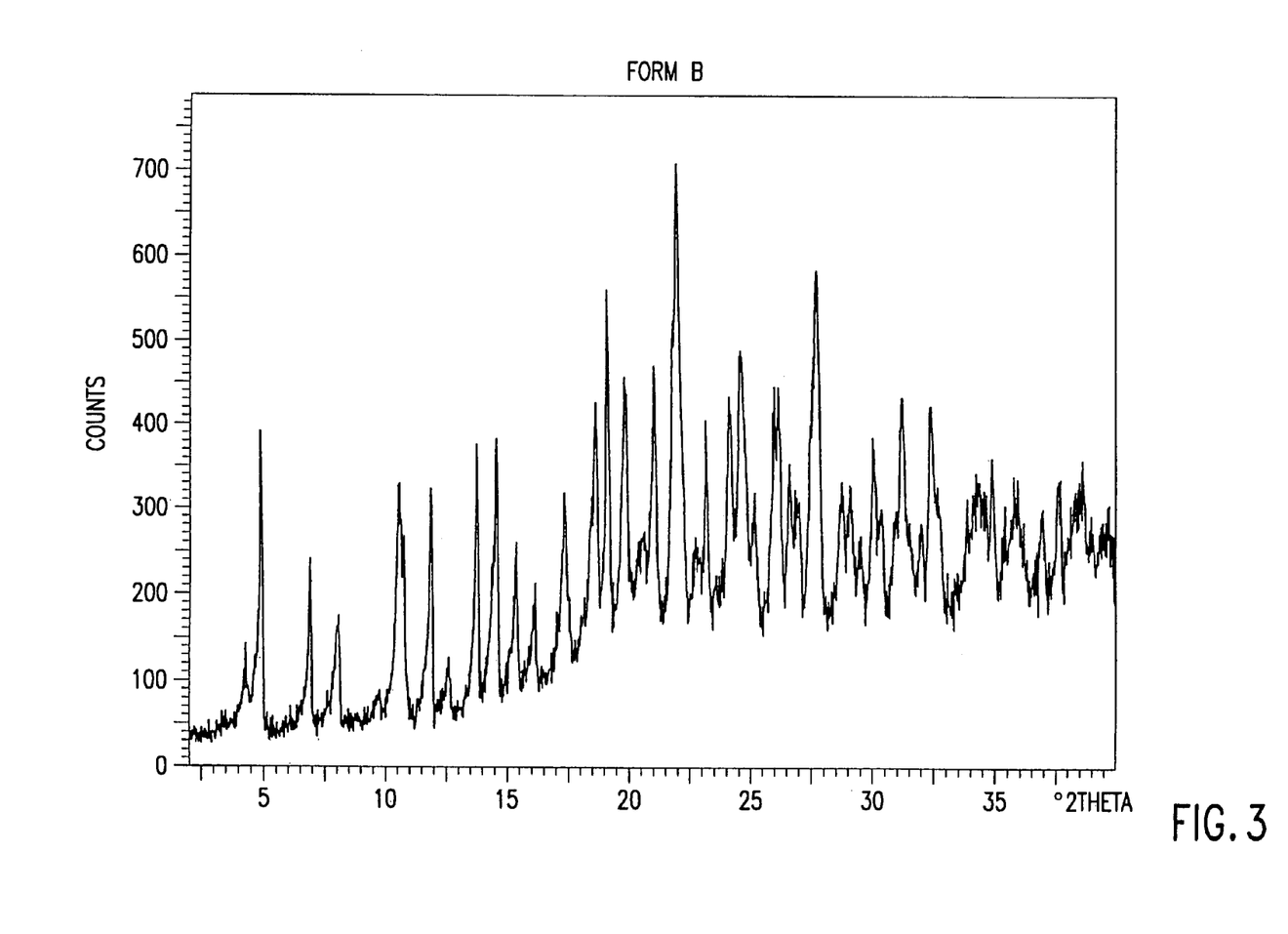
FIG. 3 is the X-Ray Powder Diffraction pattern for crystal Form B of Compound IIa after contacting 2-propanol containing 15% water.

The XRPD pattern corresponding to Table 2 is shown in FIG. 3.

Figure 4:
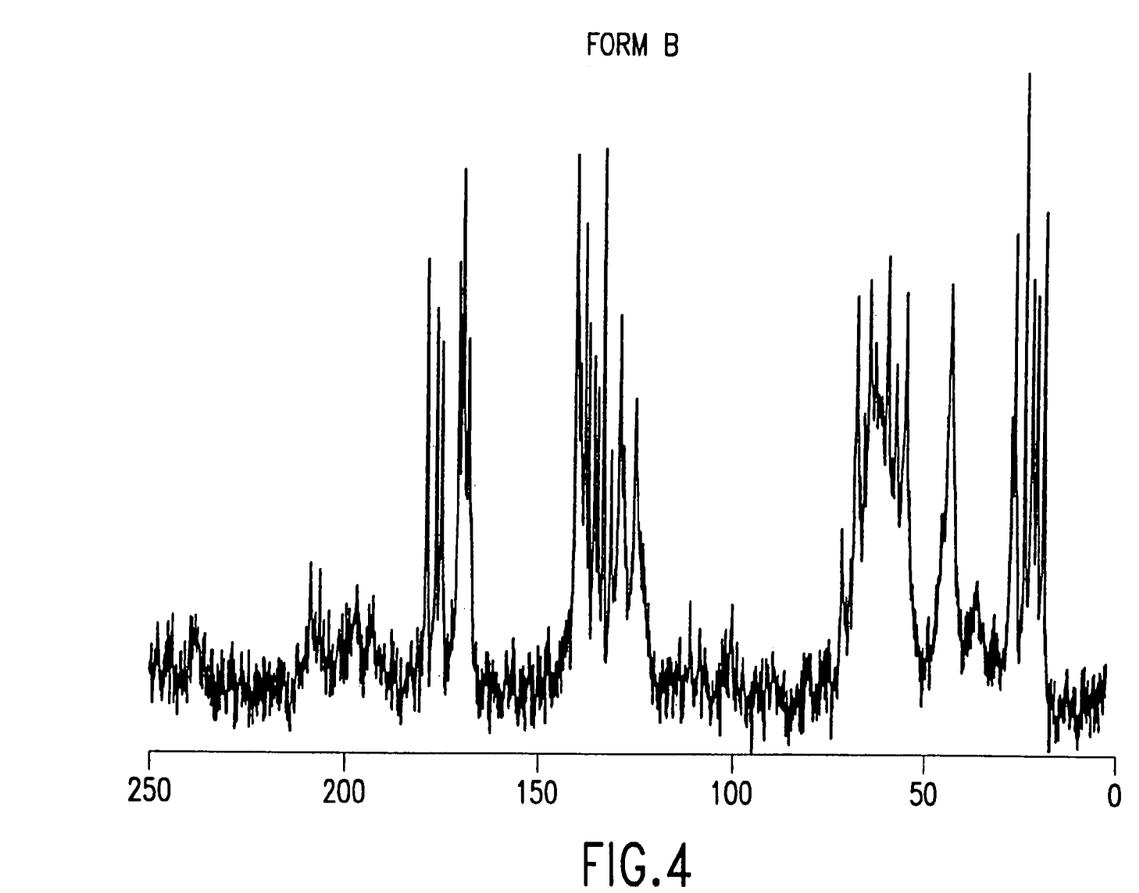
FIG. 4 is the solid-state NMR spectrum for crystal Form B of Compound IIa after contacting 2-propanol containing 15% water.

The solid-state NMR pattern corresponding to Form B is shown in FIG. 4.

Form C:

The crystalline Form C of the compound of formula IIa, which results from washing with methyl acetate or acetone containing 2 to 4% (w/v) water, is unambiguously characterized as having an XRPD pattern at 18.29, 12.94, 11.25, 8.28, 7.50, 6.46, 6.08, 5.11, 4.78, 4.63, 4.45, 4.22, 4.02, 3.67, 3.41, 3.20, 2.86, and 2.75 angstroms. More complete XRPD data pertaining to the compound is shown below in Table 3.

TABLE 3

XRPD pattern for compound of formula IIa washed with methyl acetate or acetone containing 2–3% (w/v) water (Form C).

| Angle (°2Theta) | D Spacing (angstroms) | I/Imax (%) |
|---|---|---|
| 4.8 | 18.29 | 50 |
| 6.8 | 12.94 | 22 |
| 7.8 | 11.25 | 28 |
| 10.7 | 8.28 | 65 |
| 11.8 | 7.50 | 45 |
| 13.7 | 6.46 | 44 |
| 14.6 | 6.08 | 45 |
| 17.3 | 5.11 | 30 |
| 18.6 | 4.78 | 44 |
| 19.14 | 4.63 | 67 |
| 19.9 | 4.45 | 42 |
| 21.0 | 4.22 | 35 |
| 22.1 | 4.02 | 100 |
| 24.2 | 3.67 | 60 |
| 26.1 | 3.41 | 50 |
| 27.9 | 3.20 | 59 |
| 31.3 | 2.86 | 38 |
| 32.5 | 2.75 | 39 |

The XRPD pattern corresponding to Table 3 is shown in FIG. 5.

Figure 6:
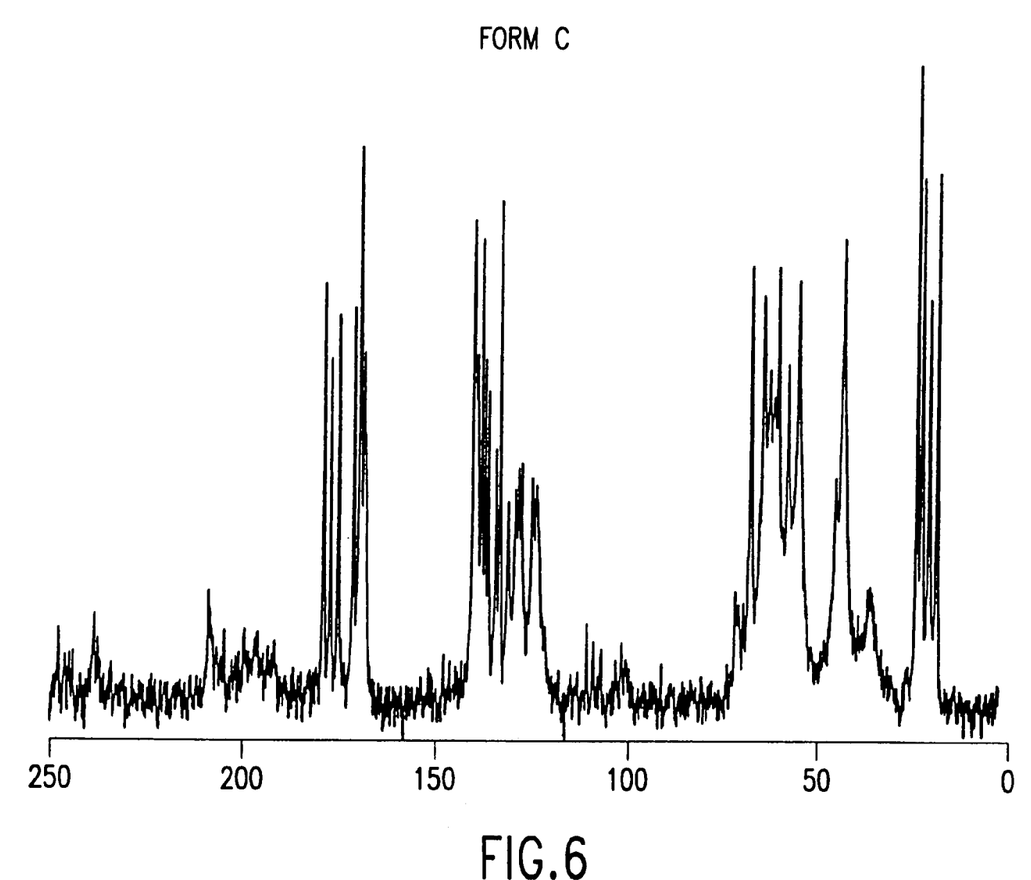
FIG. 6 is a solid-state NMR spectrum for crystal Form C of Compound IIa resulting from washing the solid containing crystal Form B of the Compound IIa with methyl acetate containing 2% (w/v) water.

The solid-state NMR spectrum for compound of formula IIa washed with methyl acetate or acetone containing 2–3% (w/v) water (Form C) is shown in FIG. 6.

The preferred process comprises washing crystalline Form B with methyl acetate containing water to give crystalline Form C. Crystalline Form C can be made from other crystalline forms of the compound of formula IIa, such as Form A, by washing Form A with an organic solvent, such as methyl acetate, containing water. Such a process would be included in the current invention.

The following examples are provided for illustrative purposes and should not be construed in any way as limiting the invention disclosed herein.

EXAMPLE 1

A hydrogenator is charged with 63 g of 5% Pd on carbon catalyst (dry weight) in 1.8 L of water. The vessel is placed under hydrogen then vented and placed under nitrogen. Sodium hydroxide (68 g, 50 wt %) is charged adjusting the pH to about 7.5 with carbon dioxide.

The enol phosphate (170 g) and the thiol (86 g) are dissolved in 1.3 L of N-ethylpyrrolidinone (NEP). The mixture is cooled to below −40° C. and 1,1,3,3-tetramethylguanidine (109 g) is added. After 3 hours, the reaction mixture is quenched into the hydrogenator at below 15° C. adjusting the pH to about 8 with carbon dioxide. The vessel is placed under hydrogen. When the reaction is complete, the hydrogen is vented and the reaction mixture is treated with activated carbon and filtered. The filtrate is extracted with iso-amyl alcohol containing diphenylphosphoric acid (240 g) and 50 wt % NaOH (44 g). The resulting aqueous solution is further extracted with iso-amyl alcohol to give an aqueous solution containing at least 90 mg/mL of the compound of formula IIa (predominantly in the stabilized form, 4). Both extractions are performed using two CINC (Costner Industries Nevada Corporation) centrifugal separators set in series for countercurrent extraction. 1-Propanol is added (20% by volume) and the resulting solution is cooled to below −5° C. The pH is adjusted to 5.5 at below −5° C. using a solution of acetic acid in methanol (3 M). Methanol and 1-propanol are added to 0.5 and 0.25 volumes total relative to the aqueous solution from the extraction. The resulting solution is seeded with a slurry containing 0.1 g of the compound of formula IIa in a mixture of water, methanol, and 1-propanol (2, 1, and 0.5 mL, respectively) prepared at −10° C. The product is then crystallized at below −5° C. by adding methanol and 1-propanol to bring the total of each to one volume relative to the aqueous solution from the extraction and isolated by filtration to give the compound of formula IIa crystalline solid (Form A). The solid is washed with a mixture of 2-propanol and water (85:15 v/v, 10 mL/assay g of compound IIa) at below 10° C. to give a compound of formula IIa as a crystalline solid (Form B).

The crystalline compound (4R, 5S, 6S, 8R, 2'S, 4'S)-3-[[2-[[3-carboxyphenyl)amino]carbonyl]-pyrrolidin-4-yl]thio]-4-methyl-6-(1-hydroxyethyl)-7-oxo-1-azabicyclo [3.2.0]hept-2-en-2-carboxylic acid sodium salt (formula IIa) derived by washing the solid with a mixture of 2-propanol containing water (85:15 v/v) with methyl acetate containing 2% (w/v) water (20 mL/assay g of compound IIa) to give a new crystalline form of the compound of formula IIa (Form C).

The crystalline material derived by washing the solid with a mixture of methyl acetate containing 2% (w/v) water (Form C) was placed under vacuum with a nitrogen sweep through the solid. The cake temperature was maintained below 7° C. The dew point of the nitrogen was at least 2° C. below the temperature of the cake during the residual solvent reduction operation. The water content of the solid was maintained between 16 and 20%. The operation was completed with dry nitrogen to give compound of formula IIa containing 16 to 22% water and less than 1.5% methyl acetate and less than 0.5% residual alcohol solvents. The loss in purity is typically 0.2 to 0.5 area % by HPLC analysis.

YMCbasic 250×4.6 mm 90:10 to 60:40 (v/v) 0.05% $H_3PO_4$:acetonitrile over 20 minutes then hold for 5 min; 1.0 mL/min; UV @ 225 nm; retention time=10.3 min. UV (nm, $H_2O$) 294; FT-IR (Nujol™ mull, cm$^{-1}$) 3650–3600, 1751, 1695, 1559, 1459, 1377, 771; $^1$H NMR (500.13 MHz, $D_2O$ with internal dioxane as reference at δ=3.75) δ 7.86 (m, 1H), 7.71 (m, 1H), 7.65 (m, 1H), 7.47 (t, 1H, J=8.0 Hz), 4.62 (t, 1H, J=8.3 Hz), 4.21 (om, 1H), 4.18 (dd, 1H, J=9.5, 2.4 Hz), 4.07 (m, 1H), 3.82 (dd, 1H, J=12.3, 6.8 Hz), 3.47 (dd, 1H, J=12.3, 5.6 Hz), 3.42 (dd, 1H, J=6.0, 2.4 Hz), 3.31 (m, 1H), 3.02 (m, 1H), 2.20 (m, 1H), 1.27 (d, 3H, J=6.4 Hz), 1.17 (d, 3H, J=6.8 Hz); $^{13}$C NMR (100.61 MHz, $D_2O$) δ 177.3, 175.3, 168.4, 167.7, 138.4, 138.1, 137.0, 134.5, 130.0, 127.0, 124.9, 122.5, 65.9, 60.9, 59.5, 56.7, 53.2, 43.5, 41.4, 35.5, 20.9, 16.7; FTICR/MS calculated for $[C_{22}H_{25}N_3O_7S+H]^+$: 476.1486; found: 476.1498.

EXAMPLE 2

4R, 5S, 6S, 8R, 2'S, 4'S)-3-[[2-[[3-carboxyphenyl)amino]carbonyl]pyrrolidin-4-yl]thio]-4-methyl-6-(1-hydroxyethyl)-7-oxo-1-azabicyclo[3.2.0]hept-2-en-2-carboxylic acid sodium salt Form B (31.6 g containing 22% 2-propanol, 20.1 assay g) was slurried in 50 mL of methyl acetate containing 4% (w/v) water at 4° C. for 0.5 h. The solvent was drained to bed height and the cake was slurried in 50 mL of methyl acetate containing 4% (w/v) water at 4° C. for 1.5 h. The solid was then washed with 3×50 mL of methyl acetate containing 4% (w/v) water. Dry nitrogen was passed through the solid using vacuum to maintain a flow of 200–500 mL/min (0.6–1.5 SLPH/assay gram of the compound). The solids were stirred intermittently. After about 3 h, the level of methyl acetate had been reduced to less than 1% and 2-propanol was undetected (<0.05%). Less than 0.2 area % loss in purity was observed by HPLC analysis.

EXAMPLE 3

4R, 5S, 6S, 8R, 2'S, 4'S)-3-[[2-[[3-carboxyphenyl)amino]carbonyl]pyrrolidin-4-yl]thio]-4-methyl-6-(1-hydroxyethyl)-7-oxo-1-azabicyclo[3.2.0]hept-2-en-2-carboxylic acid sodium salt Form A obtained by crystallization of 6.8 g of the monosodium salt from a mixture of water, methanol, and 1-propanol (1:1.25:1.25 v/v/v) was washed with 4×50 mL of acetone containing 5% (w/v) water at 9° C. Humidity-controlled nitrogen (dew point <0° C.) was then passed through the solid reducing the level of acetone to less than 0.5%. Methanol and 1-propanol were undetected (<0.05%). The water content of samples taken during the operation was 15 to 19%. Less than 0.3 area % loss in purity was observed by HPLC analysis.

EXAMPLE 4

4R, 5S, 6S, 8R, 2'S, 4'S)-3-[[2-[[3-carboxyphenyl)amino]carbonyl]pyrrolidin-4-yl]thio]-4-methyl-6-(1-hydroxyethyl)-7-oxo-1-azabicyclo[3.2.0]hept-2-en-2-carboxylic acid sodium salt Form B (5.5 kg, 2-propanol 17.3%, 1-propanol 0.3%, methanol 0.02%, water 12.3%, 99.1 area % pure by HPLC) was charged to a Cogeim agitated filter dryer. Dry nitrogen, cooled to 12–14° C., was passed through the solid at 5 SLPH/assay gram of the compound of formula IIa for about 7 h (jacket 3° C., solid temperature 6–7° C.). The nitrogen flow was adjusted to 7 SLPH/assay gram of the compound and the dew point was controlled at −2 to 2° C. reducing the level of residual 2-proponal to 0.4% (water content 14%). Total time for residual organic solvent reduction was about 50 h. This process typically results in about 1 area % loss in purity as observed by HPLC analysis.

EXAMPLE 5

4R, 5S, 6S, 8R, 2'S, 4'S)-3-[[2-[[3-carboxyphenyl)amino]carbonyl]pyrrolidin-4-yl]thio]-4-methyl-6-(1-hydroxyethyl)-7-oxo-1-azabicyclo[3.2.0]hept-2-en-2-carboxylic acid sodium salt isolated by crystallization from water, methanol, and 1-propanol (about 1.2 assay kg, 98.7 area % pure by HPLC) was washed with 4 L of a 90:10 mixture of ethanol and water precooled to below 0° C. in a 12 in diameter filter pot. The solid was then washed with 12 L of anhydrous ethanol at ambient temperature. Vacuum under the filterplate was adjusted to achieve a flow of nitrogen through the cake of about 3 SLPH/assay gram of the compound of formula IIa. After 4 h, the solid was a free-flowing powder containing 19% ethanol and 1% water with methanol and 1-propanol undetected (purity 98.5 area % by HPLC). The relative humidity of the nitrogen stream was adjusted to 40 to 60% at ambient temperature. After 13.5 h, the level of ethanol had been reduced to 0.8%. The purity was 97.2 area % by HPLC analysis.

What is claimed is:

1. A process for reducing the levels of organic solvents in a crystalline carbapenem to pharmaceutically acceptable levels, comprising washing the crystalline carbapenem containing organic solvent with an organic solvent containing water to produce a washed carbapenem solid containing residual organic solvent; wherein throughout the washing the water content of the crystalline carbapenem solids, correcting for residual organic solvents, is maintained at about 13% to about 25% and evaporating the residual organic solvent in the washed carbapenem solid using vacuum and/or inert gas at low temperature to produce a crystalline carbapenem solid containing pharmaceutically acceptable levels of residual organic solvents, wherein the water content of the crystalline carbapenem solids throughout evaporation, correcting for residual organic solvents, is maintained at about 13% to about 25%, wherein the organic solvent is selected from the group consisting of methanol, ethanol, 1-propanol, 2-propanol, methyl acetate, ethyl acetate, isopropyl acetate, acetone, and methyl ethyl ketone or mixture thereof and the organic solvent containing water is selected from the group consisting of methyl acetate, acetonitrile, tetrahydrofuran, and acetone or a mixture thereof.

2. A process for reducing the levels of organic solvents in a carbapenem solid of formula I:

or salts thereof, wherein $R_1$ and $R_2$ are the same or different and are selected from H, alkyl, aryl, and heteroaryl, said alkyl, aryl and heteroaryl optionally substituted, comprising the steps of:
   a) washing the carbapenem solid containing organic solvent with an organic solvent containing water to produce a washed carbapenem solid containing residual organic solvent; and
   b) evaporating the residual organic solvent in the washed carbapenem solid using vacuum and/or an inert gas stream at low temperature to produce a carbapenem solid of formula I containing pharmaceutically acceptable levels of organic solvents, wherein the organic solvent is selected from the group consisting of methanol, ethanol, 1-propanol, 2-propanol, methyl acetate, ethyl acetate, isopropyl acetate, acetone, and methyl ethyl ketone or mixture thereof and the organic solvent containing water is selected from the group consisting of methyl acetate, acetonitrile, tetrahydrofuran, and acetone or a mixture thereof.

3. A process according to claim 2 wherein the temperature is about –15° C. to about 20° C. and the water content of the carbapenem solids is maintained at about 13% to about 25%, correcting for residual organic solvent throughout the washing and evaporating steps.

4. The process according to claim 3 wherein the water content of the carbapenem solids during the process is maintained at about 16% to about 22%.

5. The process according to claim 2 wherein the evaporation step is conducted under vacuum at temperatures below about 0° C.; using an inert gas stream at temperatures below about 0° C.; under vacuum with an inert gas stream at temperatures below about 0° C. or using a hydrated inert gas stream to maintain the water content of the solids at about 16 to about 22% throughout the washing and evaporating steps.

6. The process according to claim 2 wherein the organic solvent containing water is selected from the group consisting of methyl acetate, acetonitrile, tetrahydrofuran, and acetone or a mixture thereof containing about 1% to about 5% (w/v) water.

7. The process according to claim 6 wherein the organic solvent is methyl acetate containing about 2% to about 4% (w/v) water.

8. A process for reducing the levels of residual organic solvents to pharmaceutically acceptable levels in a carbapenem solid of formula II:

wherein $X^+$ is selected from $Na^+$, $K^+$, and $Li^+$, comprising the steps of:
   a) washing the carbapenem solid of formula II containing organic solvent with an organic solvent containing water selected from the group consisting of acetone, acetonitrile, tetrahydrofuran, methyl acetate or a mixture thereof; said organic solvent containing about 1% to about 5% (w/v) water to produce a washed carbapenem solid of formula II containing residual organic solvent; and
   b) evaporating the residual organic solvent in the washed carbapenem solid of formula II using vacuum and/or inert gas at a temperature of about –15° C. to about 20° C. to produce a carbapenem solid of formula II containing pharmaceutically acceptable levels of residual organic solvent.

9. A process according to claim 8 wherein the organic solvent is selected from the group consisting of methanol, ethanol, 1-propanol, and 2-propanol or mixture thereof; the organic solvent containing water is methyl acetate containing about 2% to about 4% (w/v) water; and the water content of the carbapenem compound is maintained at about 13% to about 25% throughout the washing and evaporating steps.

10. The process according to claim 8 wherein the evaporation step is conducted under vacuum at temperatures below about 0° C.; using an inert gas stream at temperatures below about 0° C.; or under vacuum with an inert gas stream at temperatures below about 0° C.

11. The process according to claim 10 wherein when using an inert gas stream, the inert gas stream is nitrogen gas and the flow rate of the inert gas stream is about 0.3 to about 30 SLPH (standard liters/hour)/assay gram of the compound of formula II.

12. The process according to claim 11 wherein the inert gas stream used in residual solvent reduction is hydrated such that the water content of the solid is maintained at about 13% to about 25% throughout the washing and evaporating steps.

13. A process for reducing the levels of organic solvents in a carbapenem solid of(4R, 5S, 6S, 8R, 2'S, 4'S)-3-[[2-[[3-carboxyphenyl)amino]-carbonyl]pyrrolidin-4-yl]thio]-4-methyl-6-(1-hydroxyethyl)-7-oxo-1-azabicyclo[3.2.0]hept-2-en-2-carboxylic acid monosodium salt represented by formula IIa:

comprising the steps of:
   a) washing the carbapenem solid of formula IIa containing organic solvent with methyl acetate containing 1–5% (w/v) water to produce a washed carbapenem solid of formula IIa containing residual organic solvent; and
   b) evaporating the residual organic solvent in the washed carbapenem solid of formula IIa under vacuum using a hydrated nitrogen stream at a nitrogen flow rate of about 0.3 to about 30 SLPH (standard liters/hour)/assay gram of the compound and a temperature of about 10° C. or below to produce a carbapenem solid of formula IIa containing pharmaceutically acceptable levels of residual organic solvents.

14. A process according to claim 13 wherein the organic solvent is selected from the group consisting of methanol, ethanol, 1-propanol, and 2-propanol or mixture thereof; the methyl acetate contains about 2% to about 4% (w/v) water;

and the water content of the carbapenem solids is maintained at about 13% to about 25% throughout the washing and evaporating steps.

15. A process for reducing the levels of residual organic solvents in a carbapenem solid of (4R, 5S, 6S, 8R, 2'S, 4'S)-3-[[2-[[3-carboxyphenyl)amino]-carbonyl]pyrrolidin-4-yl]thio]-4-methyl-6-(1-hydroxyethyl)-7-oxo-1-azabicyclo[3.2.0]hept-2-en-2-carboxylic acid monosodium salt having Form C of FIG. 5 and represented by formula IIa:

IIa comprising evaporating the residual organic solvent using vacuum and a hydrated nitrogen stream at a nitrogen flow rate of about 0.3 to about 30 SLPH (standard liters/hour)/assay gram of the compound and a temperature of about 10° C. or below to produce a carbapenem solid of formula IIa containing pharmaceutically acceptable levels of residual organic solvents.

16. The process according to claim 15 wherein the residual organic solvent is selected from the group consisting of methanol, ethanol, 1-propanol, 2-propanol, methyl acetate, acetonitrile, tetrahydrofuran, and acetone or a mixture thereof; and the water content of the carbapenem compound is maintained at about 13% to about 25% throughout the washing and evaporating steps.

17. A process for making a novel crystalline hydrate, Form C of FIG. 5, of the compound of formula IIa:

IIa comprising washing a crystalline carbapenem of Form A of FIG. 3 or Form B of FIG. 4 with an organic solvent selected from methyl acetate, acetone or a mixture thereof containing water and isolating crystalline hydrate Form C of the carbapenem solid of formula IIa.

18. The process according to claim 17 wherein the crystalline compound is Form B and the organic solvent used in washing the carbapenem solid, Form B, is methyl acetate containing 2% to about 4% water.

19. A process for reducing the levels of organic solvents in carbapenem solids of formula I:

I or salts thereof, wherein $R_1$ and $R_2$ are the same or different and are selected from H, alkyl, aryl, and heteroaryl, said alkyl, aryl and heteroaryl optionally substituted, comprising the steps of:

a) washing the carbapenem solid containing organic solvent with an anhydrous organic solvent to produce a washed carbapenem solid containing residual organic solvents; and b) evaporating the residual organic solvents in the washed carbapenem solid using vacuum and a hydrated inert gas stream at a temperature of about 20° C. or below to produce a carbapenem solid of formula I containing pharmaceutically acceptable levels of organic solvents, said inert gas stream hydrated in such a way to achieve the water content of the solids to a level of about 13 to about 25% throughout the washing and evaporating steps; wherein the organic solvent is selected from the group consisting of methanol, ethanol, 1-propanol, 2-propanol, methyl acetate, ethyl acetate, isopropyl acetate, acetone, and methyl ethyl ketone or mixture thereof; and the anhydrous organic solvent is selected from the group consisting of methanol, ethanol, 1-propanol, 2-propanol, methyl acetate, and acetone or a mixture thereof.

20. A process according to claim 19 wherein the hydrated inert gas is nitrogen.

21. Crystalline hydrate, (4R, 5S, 6S, 8R, 2'S, 4'S)-3-[[2-[[3-carboxyphenyl)amino]carbonyl]pyrrolidin-4-yl]thio]-4-methyl-6-(1-hydroxyethyl)-7-oxo-1-azabicyclo[3.2.0]hept-2-en-2-carboxylic acid monosodium salt of Form C of FIG. 5, represented by the compound of formula IIa:

which is characterized by a solid state X-ray powder diffraction XRPD pattern having the following d-spacings 18.29, 12.94, 11.25, 8.28, 7.50, 6.46, 6.08, 5.11, 4.78, 4.63, 4.45, 4.22, 4.02, 3.67, 3.41, 3.20, 2.86, and 2.75 angstroms.

* * * * *